(12) United States Patent
Bondy et al.

(10) Patent No.: US 8,263,612 B2
(45) Date of Patent: Sep. 11, 2012

(54) VIRAL INHIBITORS

(75) Inventors: Steven S. Bondy, Danville, CA (US); David A. Oare, Belmont, CA (US); Gerhard Puerstinger, Igls (AT)

(73) Assignees: Gilead Sciences, Inc., Foster City, CA (US); K.U. Leuven Research & Development, Leuven (BE); Gerhard Puerstinger, Igls (AT)

( * ) Notice: Subject to any disclaimer, the term of this patent is extended or adjusted under 35 U.S.C. 154(b) by 1040 days.

(21) Appl. No.: 11/957,017

(22) Filed: Dec. 14, 2007

(65) Prior Publication Data

US 2008/0207678 A1 Aug. 28, 2008

Related U.S. Application Data

(60) Provisional application No. 60/874,797, filed on Dec. 14, 2006.

(51) Int. Cl.
*C07D 487/04* (2006.01)
*A61K 31/437* (2006.01)

(52) U.S. Cl. ........ 514/300; 546/113

(58) Field of Classification Search ........ 514/300; 546/113
See application file for complete search history.

(56) References Cited

U.S. PATENT DOCUMENTS

2006/0052602 A1 3/2006 Kim et al.

FOREIGN PATENT DOCUMENTS

| JP | 04358143 | * | 12/1992 |
| WO | WO-2005/063744 A2 | | 7/2005 |
| WO | WO-2006/069193 A2 | | 6/2006 |

OTHER PUBLICATIONS

West, Anthony R., Solid State Chemistry and its Applications, Wiley, New York, 1988, pp. 358 & 365.*
Barraclough, P. (1990) "Inotropic Activity of Heterocyclic Analogus of Isomazole," *Europ. J. Med. Chem.* 25:467-477.
Chi et al. (2000) "Palladium-Catalyzed Functionalization of 5- and 7-Azaindoles," *Tetrahedron Letters* 41(6):919-922.
Fisher et al. (1972) "Azaindole Anthelmintic Agents," *Journal of Medicinal Chemistry, US American Chemical Society* 15(11):1168-1171.
Gallou et al. (2005) "Regioselective Halogenation of 6-Azaindoles: Efficient Synthesis of 3-Halo-2, 3-Disubstituted-6-Azaindole Derivatives," *Synlett* 15:2400-2402.
Hands et al. (1996) "A Convenient Method for the Preparation of 5-, 6- amd 7-Azaindoles and Their Derivatives," *Synthesis* pp. 877-882.
Harcken et al. (2005) "A General and Efficient Synthesis of Azaindoles and Diazaindoles," *Synlett* 20:3121-3125.
Ujjainwalla et al. (1998) "Synthesis of 5-l, or 6- and 7-Azaindoles via Pailladium-Catalyzed Catalyzed Heteroarinulation of Internal Alkynes," *Tetrahderon Letters* 39(30):5355-5358.
International Search Report and Written Opinion for PCT/US2007/025689, International Filing Date of Dec. 14, 2007.

* cited by examiner

*Primary Examiner* — Niloofar Rahmani
(74) *Attorney, Agent, or Firm* — Clark & Elbing LLP

(57) ABSTRACT

Pyrrolo[2,3-c]pyridine or pyrrolo[3,2-c]pyridine compounds having the general formula (A),

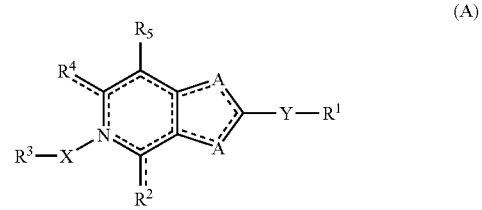

wherein the dashed lines, X, Y and $R^1$ through $R^5$ are as defined in the specification. The compounds are useful in the prophylaxis or treatment of viral infections.

18 Claims, No Drawings

VIRAL INHIBITORS

This non-provisional application claims the benefit of Provisional Application No. 60/874,797, filed Dec. 14, 2006, which is incorporated herein by reference.

FIELD OF THE INVENTION

The present invention relates to a series of novel pyrrolo[2,3-c]pyridines and pyrrolo[3,2-c]pyridines, processes for their preparation, their use to treat or prevent viral infections and their use to manufacture a medicine to treat or prevent viral infections, particularly infections with viruses belonging to the family of the Flaviviridae and more preferably infections with hepatitis-C-virus (HCV).

BACKGROUND OF THE INVENTION

The World Health Organization estimates that world-wide 170 million people (3% of the world's population) are chronically infected with HCV. These chronic carriers are at risk of developing cirrhosis and/or liver cancer. In studies with a 10 to 20 year follow-up, cirrhosis developed in 20-30% of the patients, 1 to 5% of whom may develop liver cancer during the next then years. The only treatment option available today is the use of interferon α-2 (or its pegylated form) either alone or combined with ribavirin. However, sustained response is only observed in about 40% of the patients and treatment is associated with serious adverse effects. There is thus an urgent need for potent and selective inhibitors of the replication of the HCV in order to treat infections with HCV. Furthermore, the study of specific inhibitors of HCV replication has been hampered by the fact that it is not possible to propagate HCV (efficiently) in cell culture. Since HCV and pestiviruses belong to the same virus family and share many similarities (organization of the genome, analogous gene products and replication cycle), pestiviruses have been adopted as a model and surrogate for HCV. For example BVDV is closely related to hepatitis C virus (HCV) and used as a surrogate virus in drug development for HCV infection.

In view of their important pharmacological value, there is a need for drugs having antiviral activity, optionally selective activity against viruses belonging to the family of Flaviviridae including hepatitis C virus, and against viruses belonging to the family of Picornaviridae.

SUMMARY OF THE INVENTION

The invention relates to the use of pyrrolo[2,3-c]pyridines and pyrrolo[3,2-c]pyridines, as antiviral compounds, more particularly as compounds active against HCV, which correspond to the general formula (A),

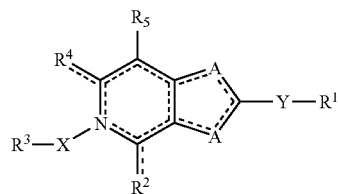

(A)

wherein:
the dotted lines represent at least 3, optionally 4 double bonds, provided that no two double bonds are adjacent to one another;

A is —N= or $CR^{26}$, but one A is $CR^{26}$;

$R^1$ is selected from hydrogen, aryl, heterocycle, $C_1$-$C_{10}$ alkoxy, $C_1$-$C_{10}$ thioalkyl, $C_1$-$C_{10}$ alkyl-amino, $C_1$-$C_{10}$ dialkyl-amino, $C_{3-10}$ cycloalkyl, $C_{4-10}$ cycloalkenyl, and $C_{4-10}$ cycloalkynyl, wherein each are optionally substituted with 1 to 3 $R^6$;

Y is selected from a single bond, O, $S(O)_m$, $NR^{11}$, $C_{1-10}$ alkylene, $C_{2-10}$ alkenylene, or $C_{2-10}$ alkynylene, wherein 1 to 3-C(H)=, —C(=) or —CH$_2$— groups of each alkylene, alkenylene or alkynylene optionally are independently replaced with a heteroatom or heteroatom group selected from —O—, =O, —OR$^{27}$, —S—, =S, —SR$^{27}$, —NR$^{27}$, —N(R$^{27}$)$_2$ where $R^{27}$ independently is hydrogen, $C_{1-18}$ alkyl, $C_{2-18}$ alkenyl, or $C_{2-18}$ alkynyl;

provided that $YR^1$ is not hydrogen or $C_{1-6}$ alkyl;

$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{3-10}$ cycloalkynyl, or heterocycle;

X is absent or is selected from hydrogen, $C_1$-$C_{10}$ alkylene, $C_{2-10}$ alkenylene or $C_{2-10}$ alkynylene, wherein 1 to 3-C(H)=, —C(-) or —CH$_2$— groups of each alkylene, alkenylene or alkynylene optionally are independently replaced with a heteroatom or heteroatom group selected from —O—, =O, —OR$^{27}$, —S—, =S, —SR$^{27}$, —NR$^{27}$, —N(R$^{27}$)$_2$ where $R^{27}$ independently is hydrogen, $C_{1-18}$ alkyl, $C_{2-18}$ alkenyl, or $C_{2-18}$ alkynyl, provided any such heteroatom is not adjacent to the N in the pyridinyl ring;

m is any integer from 0 to 2;

$R^3$ is absent or is selected from hydrogen, aryl, aryloxy, arylthio, cycloalkyl, cycloalkenyl, cycloalkynyl, aryl-N(R$^{10}$)—, or an aromatic heterocycle, where each said substituent is optionally substituted with 1 or more $R^{17}$, provided that for cycloalkenyl the double bond is not adjacent to a nitrogen;

$R^5$ is selected from hydrogen; $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=O)OR$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocycle;

$R^6$ is selected from hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —CO$_2$R$^{18}$, NO$_2$, —NR$^7$R$^8$, $C_{1-18}$ haloalkyl, C(=O)R$^{18}$, C(=S)R$^{18}$, SH, aryl, aryloxy, arylthio, arylsulfoxide, arylsulfone, arylsulfonamide, aryl(C$_{1-18}$)alkyl, aryl(C$_{1-18}$)alkyloxy, aryl(C$_{1-18}$)alkylthio, heterocycle and $C_{1-18}$ hydroxyalkyl, where each is optionally substituted with 1 to 3 $R^{19}$;

$R^7$ and $R^8$ are independently selected from hydrogen, $C_{1-18}$ alkyl, $C_{1-18}$ alkenyl, aryl, $C_{3-10}$ cycloalkyl, $C_{4-10}$ cycloalkenyl, heterocycle, —C(=O)R$^{12}$; —C(=S)R$^{12}$, an amino acid residue linked through a carboxyl group thereof, or $R^7$ and $R^8$ are taken together with the nitrogen to form a heterocycle;

$R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —$NR^{15}R^{16}$, aryl, an amino acid residue linked through an amino group of the amino acid, $CH_2OCH(=O)R^{9a}$, or $CH_2C(=O)OR^{9a}$ where $R^{9a}$ is $C_1$-$C_{12}$ alkyl, $C_6$-$C_{20}$ aryl, $C_6$-$C_{20}$ alkylaryl or $C_6$-$C_{20}$ aralkyl;

$R^{10}$ and $R^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —$C(=O)R^{12}$, heterocycle, or an amino acid residue;

$R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, or an amino acid residue;

$R^{15}$ and $R^{16}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, or an amino acid residue;

$R^{17}$ is independently selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halogenated alkyl, $C_{2-18}$ halogenated alkenyl, $C_{2-18}$ halogenated alkynyl, $C_{1-18}$ halogenated alkoxy, $C_{1-18}$ halogenated alkylthio, $C_{3-10}$ cycloalkyl, $C_{3-10}$ cycloalkenyl, $C_{7-10}$ cycloalkynyl, halogen, OH, CN, $CO_2H$, $CO_2R^{18}$, $NO_2$, $NR^7R^8$, haloalkyl, $C(=O)R^{18}$, $C(=S)R^{18}$, SH, aryl, aryloxy, arylthio, arylsulfoxide, arylsulfone, arylsulfonamide, arylalkyl, arylalkyloxy, arylalkylthio, heterocycle, $C_{1-18}$ hydroxyalkyl, where each of said aryl, aryloxy, arylthio, arylsulfoxide, arylsulfone, arylsulfonamide, arylalkyl, arylalkyloxy, arylalkylthio, heterocycle, or $C_{1-18}$ hydroxyalkyl is optionally substituted with 1 or more $R^{19}$;

$R^{19}$ is selected from hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, $C_{4-10}$ cycloalkynyl, halogen, —OH, —CN, cyanoalkyl, —$NO_2$, —$NR^{20}R^{21}$, $C_{1-18}$ haloalkyl, $C_{1-18}$ haloalkyloxy, —$C(=O)R^{18}$, —$C(=O)OR^{18}$, —$OalkenylC(=O)OR^{18}$, —$OalkylC(=O)NR^{20}R^{21}$, —$OalkylOC(=O)R^{18}$, —$C(=S)R^{18}$, SH, —$C(=O)N(C_{1-6}$ alkyl), —$N(H)S(O)(O)(C_{1-6}$ alkyl), aryl, heterocycle, $C_{1-18}$alkylsulfone, arylsulfoxide, arylsulfonamide, aryl($C_{1-18}$)alkyloxy, aryloxy, aryl($C_{1-18}$ alkyl) oxy, arylthio, aryl($C_{1-18}$)alkylthio or aryl($C_{1-18}$)alkyl, where each is optionally substituted with 1 to 3 of =Q, $NR^{20}R^{21}$, CN, $C_{1-18}$ alkoxy, heterocycle, $C_{1-18}$ haloalkyl, heterocycle alkyl, heterocycle connected to $R^{17}$ by alkyl, alkoxyalkoxy or halogen;

$R^{20}$ and $R^{21}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, —$C(=O)R^{12}$, or —$C(=S)R^{12}$;

$R^{26}$ is independently selected from hydrogen, $C_{1-18}$ alkyl, $C_{3-10}$ cycloalkyl, aryl, heterocycle, where each is optionally independently substituted with 1 to 3 of $C_{1-6}$ alkyl, $C_{1-6}$ alkoxy, halo, $CH_2OH$, benzyloxy, and OH; and salts, tautomers, stereoisomers and solvates thereof.

The invention further relates to the use of the formula (A) compounds in the prophylaxis or treatment of viral infections. They inhibit HCV and are believed to be active against BVDV, HCV and Coxsackie virus infections as well. The compounds of this invention are useful in the manufacture of a medicament for the treatment of these and other retroviral or lentiviral infections. Therefore, these compounds constitute a new potent class of anti-viral compounds having pharmaceutically desirable toxicity, bioavailability and other pharmacological properties making them useful in the treatment and prevention of viral infections in animals, mammals and humans, more specifically for the treatment and prevention of HCV virus infections.

The invention also relates to methods for preparation of such compounds and pharmaceutical compositions comprising them.

DETAILED DESCRIPTION OF THE INVENTION

The physiologically acceptable salts of the compounds of the invention include salts derived from an appropriate base, such as an alkali metal (for example, sodium), an alkaline earth (for example, magnesium), ammonium and $NX^{4+}$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX^{4+}$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

The double bonds in formula (A) are depicted as facultative bonds. The pyrrolopyridine core ring structures of the compounds of formula (A) have 3 or optionally 4 double bonds. All tautomeric positions possible for these bonds are intended to be represented by this depiction. The stable positions of these bonds will depend upon their number and the positions and identities of the other substituents on the nucleus, as will be understood by those skilled in the art.

"Alkyl" is a normal, secondary, tertiary or cyclic hydrocarbon containing 1 to 18 carbon atoms. The acyclic alkyl typically contains 1 to 6 carbon atoms. Cycloalkyl usually contains 3 to 6 carbon atoms and consists of 1 or 2 rings. Examples of "alkyl" include methyl, ethyl, 1-propyl, 2-propyl, 1-butyl, 2-methyl-1-propyl(t-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl, cyclopropyl, cyclobutyl, cyclopentyl, cycloheptyl, cyclooctyl and the like, or a $C_{7-10}$ polycyclic saturated hydrocarbon radical having from 7 to 10 carbon atoms such as, for instance, norbornyl, fentyl, trimethyltricycloheptyl or adamantyl.

"Alkenyl" is a normal, secondary, tertiary or cyclic hydrocarbon group containing 1 to 3 double bonds and 3 to 18 carbon atoms. The acyclic portion typically contains 1 to 3 carbon atoms, and each cyclic portion usually contains 3 to 6 carbon atoms. Examples include, but are not limited to, ethylene or vinyl (—CH=$CH_2$), allyl (—$CH_2CH$=$CH_2$), cyclopentenyl (—$C_5H_7$), 5-hexenyl (—$CH_2CH_2CH_2CH_2CH$=$CH_2$), 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. The double bond optionally is in the cis or trans configuration.

"Alkynyl" is a normal, secondary, tertiary or cyclic hydrocarbon group containing 1 to 3 triple bonds and 3 to 18 carbon atoms. Examples include, but are not limited to, —C≡CH, —CH$_2$C≡CH, —CH$_2$C≡C-cyclohexyl, or —CH$_2$-cycloheptenyl.

The suffix "-ene" used in connection with alkyl, alkenyl and alkynyl groups refers to such groups with at least 2 sites of substitution. Such polyvalent hydrocarbon radicals include, but are not limited to, methylene (—CH$_2$—) 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), 1,2-ethylene (—CH=CH—), —C☐C—, propargyl (—CH$_2$C☐C—), and 4-pentynyl (—CH$_2$CH$_2$CH$_2$C☐CH—).

"Aryl" means an aromatic hydrocarbon containing 1 or more rings, generally 1, 2 or 3, with 4 to 6 carbon atoms in each, ordinarily 5 or 6 carbon atoms.

"Arylalkyl," "arylalkenyl" and "arylalkynyl" means an alkyl, alkenyl or alkynyl radical, respectively, in which one of the hydrogen atoms, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

As noted, carbocycles optionally are found as single rings or multiple ring systems. Ordinarily the hydrocarbons of the compounds of formula (A) are single rings. Monocyclic carbocycles generally have 3 to 6 ring atoms, still more typically 5 or 6 ring atoms. Bicyclic carbocycles typically have 7 to 12 ring atoms, e.g. arranged as a bicyclo[4,5], [5,5], [5,6] or [6,6] system, or 9 or 10 ring atoms arranged as a bicyclo [5,6] or [6,6] system.

If the number of carbon atoms is unspecified for a hydrocarbon, typically the number of carbon atoms will range from 1 to 18, except that the number of carbons typically will range from 2 to 18 for unsaturated hydrocarbons and from 6 to 10 for aryl.

"Heterocyclic" or "heterocycle" means any 4, 5, 6, 7, 8 or 9 membered single or fused ring system containing one or more heteroatoms selected from the group consisting of O, N or S. Heterocycles optionally are entirely aromatic, entirely saturated, or contain 1 or more intra-ring sites of unsaturation, typically double bonds. Multiple heterocyclic rings (one or more of which contains a heteroatom) are bridged or spiro Generally, the heterocyclic rings will be aromatic, and usually they are single rings. Heterocycles with 5 or 6 membered rings are typical. Usually, the heterocycles will contain 1 or 2 oxygen atoms with or without 1 or 2 N atoms. Also useful are heterocycles with 5 or 6 ring atoms and 1 to 3 N atoms. Monocycles are the typical choice. Examples of heterocycles include oxazacyloalkyl, morpholinyl, dioxacycloalkyl, thiacycloalkenyl, pyridyl, dihydroypyridyl, tetrahydropyridyl (piperidyl), thiazolyl, tetrahydrothiophenyl, furanyl, thienyl, pyrrolyl, pyranyl, pyrazolyl, pyrazolidinyl, pyrazolinyl, imidazolyl, tetrazolyl, benzofuranyl, thianaphthalenyl, indolyl, indolenyl, quinolinyl, isoquinolinyl, benzimidazolyl, piperidinyl, piperazinyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isothiazoledinyl, isoxazolyl, oxazolinyl, pyrazinyl, pyridazinyl, pyrimidinyl, pyrrolidinyl, pyrrolinyl, indolizinyl, isoindolyl, 3H-indolyl, 1H-indazoly, purinyl, 4H-quinolizinyl, isoquinolyl, quinolyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, oxazolidinyl, benzotriazolyl, benzisoxazolyl, oxindolyl, benzoxazolinyl, benzothienyl, benzothiazolyl and isatinoyl. Suitable heterocycles are exemplified in Rigaudy et al., Nomenclature of Organic Chemistry, Sections A-H (1979) at pp. 53-76 and Fletcher et al., Nomenclature of Organic Compounds, Adv. Chem. Ser. 126 (1974) at pp 49-64.

The location on the heterocycle which provides the point of attachment(s) to the rest of the compound of this invention is not critical, but those skilled in the art will recognize substitution sites that are optimal for compound stability and/or ease of synthesis. Carbon bonded heterocycles typically are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

Nitrogen containing heterocycles are bonded at nitrogen or a carbon, typically a carbon atom. These include, for example, position 1 of aziridine, 1-aziridyl, 1-azetedyl, 1-pyrrolyl, 1-imidazolyl, 1-pyrazolyl, 1-piperidinyl, 2-pyrroline, 3-pyrroline, 2-imidazoline, 3-imidazoline, 9-carbazole, 4-morpholine, 9-alpha or β-carboline, 2-isoindole, 2-pyrazoline and 3-pyrazoline, and by analogy, azetidine, pyrrole, pyrrolidine piperidine, piperazine, indole, pyrazoline, indoline, imidazole, imidazolidine, 1H-indazole and isoindoline. These and other N-containing heterocycles are well-known to those skilled in the art, and their linkage sites are a matter of discretion.

Sulfur containing heterocycles are bonded through carbon or sulfur. They include oxidized states such as —S(=O) (=O). In general, they are linked in the compounds of formula (A) analogous to N-containing heterocycles.

"Alkoxy", "cycloalkoxy", "aryloxy", "arylalkyloxy", "oxy heterocycle", "thioalkyl", "thiocycloalkyl", "arylthio", and "arylalkylthio" means substituents wherein an alkyl, cycloalkyl, aryl, or arylalkyl, respectively, are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like.

"Halogen" means any atom selected from the group consisting of fluorine, chlorine, bromine and iodine, but typically is fluorine or chlorine.

Any substituent designation that is found in more than one site in a compound of this invention shall be independently selected.

When a group is stated to be substituted with "one or more" of another group, this typically means 1 to 3 substituents, ordinarily 1, 2 or 3 substitutents.

Those of skill in the art will also recognize that the compounds of the invention may exist in many different protonation states, depending on, among other things, the pH of their environment. While the structural formulae provided herein may depict the compounds in only one of several possible protonation states, it will be understood that these structures are illustrative only, and that the invention is not limited to any particular protonation state—any and all protonated forms of the compounds are intended to fall within the scope of the invention.

Amino Acids

An "Amino-acid" is a radical derived from a molecule having the chemical formula $H_2N$—$CHR^{28}$—COOH, wherein $R^{28}$ is a side group of a naturally-occurring or known synthetic amino-acid. The amino acids optionally are substituted with hydrocarbon typically of 1 to 8 carbons at one or more carboxyl or amino groups, whether those groups are on the side chain or are terminal groups after linking the amino acid to the remainder of the compound of this invention.

Optionally the amino acid residue is a hydrophobic residue such as mono- or di-alkyl or aryl amino acids, cycloalkylamino acids and the like. Optionally, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included.

Generally, only one of any site in the parental molecule is substituted with an amino acid, although it is within the scope of this invention to introduce amino acids at more than one permitted site. In general, the α-amino or α-carboxyl group of the amino acid are bonded to the remainder of the molecule, i.e., carboxyl or amino groups in the amino acid side chains generally are not used to form the amide bonds with the parental compound (although these groups may need to be protected during synthesis of the conjugates).

The amino acid esters optionally are hydrolyzable in vivo or in vitro under acidic (pH<3) or basic (pH>10) conditions. Optionally, they are substantially stable in the gastrointestinal tract of humans but are hydrolyzed enzymatically in blood or in intracellular environments.

$R^{28}$ usually is $C_1$-$C_6$ alkyl or $C_1$-$C_6$ alkyl substituted with amino, carboxyl, amide, carboxyl (as well as esters, as noted above), hydroxyl, $C_6$-$C_7$ aryl, guanidinyl, imidazolyl, indolyl, sulfhydryl, sulfoxide, and/or alkylphosphate. $R^{28}$ also is nitrogen to form a proline residue taken together with the amino acid α-amino. However, $R^{28}$ is generally the side group of the naturally-occurring amino acid disclosed above, for example H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2CH_2$—S—$CH_3$, —$CH_2OH$, —$CH(OH)$—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH_2)_3$—NH—$C(NH_2)$—$NH_2$. $R^{28}$ also includes 1-guanidinoprop-3-yl, benzyl, 4-hydroxybenzyl, imidazol-4-yl, indol-3-yl, methoxyphenyl and ethoxyphenyl.

Exemplary Embodiments $R^1$ is generally aryl or aromatic heterocycle substituted with 1, 2 or 3 $R^6$ wherein $R^6$ is generally halogen, $C_{1-18}$ alkoxy, or $C_{1-18}$ haloalkyl. The heterocycle for use in $R^1$ or any other substituent herein typically will have 5 or 6 ring atoms and 1, 2 and/or 3 N, O or S atoms, typically 1, 2 or 3 N, 1 N and 1 O, or 1 or 2 N and 1 S atom in the ring. Usually, $R^1$ is phenyl substituted with 1 or 2 halogens, usually fluoro.

Y generally is a single bond, O, $C_{1-6}$ alkylene, $C_{2-6}$ alkenylene, $C_{2-6}$ alkynylene or one of said groups containing 1 to 3, usually 1, heteroatoms selected from O, S or $NR^{11}$. Examples include —$O(CH_2)_{1-5}$—, —$(CH_2)_{1-4}$—O—$(CH_2)_{1-4}$—, —S—$(CH_2)_{1-5}$—, —$(CH_2)_{1-4}$—S—$(CH_2)_{1-4}$—, —$NR^{11}$—$(CH_2)_{1-5}$—, —$(CH_2)_{1-4}$—$NR^{11}$—$(CH_2)_{1-4}$ or $C_{3-10}$ cycloalkylidene. Typically, Y is —$OCH_2$—, —$CH_2O$—, $C_{1-2}$ alkylene, $C_{2-3}$ alkenylene, $C_{2-3}$ alkynylene, O or a bond. Most typically, Y is a bond.

In general, $YR^1$ is not any one of H, an unsubstituted $C_{3-10}$ cycloalkyl or C1-C6 alkyl. Typically $YR^1$ is halo or halomethyl-substituted (typically trihalomethyl)phenyl. These substituents are usually in ortho or meta positions, and usually there are 1 or 2 of them.

X usually is alkylene, alkynylene or alkenylene, typically alkylene. These hydrocarbons also optionally have an intra-chain heteroatom, typically O or S. Examples include —$CH_2$—, —$CH(CH_3)$—, —$CH_2$—$CH_2$—, —$CH_2$—$CH_2$—$CH_2$—, —$CH_2$—$CH_2$—$CH_2$—$CH_2$, —$(CH_2)_{2-4}$—O—$(CH_2)_{2-4}$—, —$(CH_2)_{2-4}$—S—$(CH_2)_{2-4}$—, —$(CH_2)_{2-4}$—$NR^{10}$—$(CH_2)_{2-4}$—, $C_{3-10}$ cycloalkylidene, $C_{2-6}$ alkenylene (such as —CH=CH—$CH_2$—) and $C_{2-6}$ alkynylene. Usually, X is 1 to 3 carbons, most usually methylene.

$R^3$ generally is aryl or a heterocycle, typically an aromatic heterocycle. The heterocycle generally will contain 1, 2 or 3 N, S or O atoms in the ring, usually is linked to X through a ring carbon atom and typically contains 4 to 6, usually 5, total ring atoms. The $R^3$ aryl or heterocycle ordinarily is substituted with 1, 2 or 3, usually 1, $R^{17}$. $R^3$ optionally is not indolyl. $R^3$ is typically a heterocyclic ring shown in Table 1, e.g. oxazolyl, etc. $R^3$ generally is bonded to X via a ring carbon atom. It usually is bonded to $R^{17}$ through a ring carbon as well, but may be bonded through a ring nitrogen when the ring contains 3 N atoms. Usually, $R^{17}$ is distal to X, i.e., these two groups are positioned on substantially the opposite sides of $R^3$.

When $R^3$ is substituted with $R^{17}$ then $R^{17}$ typically is aryl or a heterocycle further substituted with 1, 2 or 3 $R^{17}$.

$R^{17}$ typically is selected from the group consisting of $C_{3-10}$ cycloalkyl, $C_{3-10}$ cycloalkenyl, $C_{7-10}$ cycloalkynyl, halogen, aryl, aryloxy, arylthio, arylsulfoxide, arylsulfone, arylsulfonamide, arylalkyl; arylalkyloxy (optionally a benzyloxy); arylalkylthio (optionally a benzylthio); a heterocycle; $C_{1-18}$ hydroxyalkyl, but typically is an aryl or a heterocycle (usually aromatic), and where each of said aryl, aryloxy, arylthio, arylsulfoxide, arylsulfone, arylsulfonamide, arylalkyl, arylalkyloxy, arylalkylthio, or heterocycle is optionally substituted with 1 or more $R^{19}$. Aryl here typically contains 5 or 6 ring atoms. $R^{17}$ generally is positioned distally to X. Optionally, $R^{17}$ is not $C(O)R^{18}$.

$R^9$ and $R^{18}$ typically are H, OH or alkyl. $R^{18}$ optionally is not $NR^{15}R^{16}$.

$R^5$ typically is H.

$R^6$ generally is halogen. Optionally, $R^6$ is not $C(O)R^{18}$.

$R^7$, $R^8$, $R^{10}$, $R^{11}$, $R^{13}$, $R^{14}$, $R^{15}$, $R^{16}$, $R^{20}$, $R^{21}$, $R^{23}$ and $R^{24}$ typically are independently H, halo, or $C_{1-18}$ alkyl.

$R^{12}$ and $R^{22}$ typically are independently OH or alkyl.

$R^{19}$ usually is H; $C_{1-18}$ alkyl; $C_{2-18}$ alkenyl; $C_{2-18}$ alkynyl; $C_{1-18}$ alkoxy; alkenyloxy; alkynyloxy; $C_{1-18}$ alkylthio; $C_{3-10}$ cycloalkyl; $C_{4-10}$ cycloalkenyl; $C_{4-10}$ cycloalkynyl; halogen; OH; CN; cyanoalkyl; $NO_2$; $NR^{20}R^{21}$; haloalkyl; haloalkyloxy; $C(=O)R^{18}$; $C(=O)OR^{18}$; $OalkenylC(=O)OR^{18}$;

—OalkylC(=O)NR$^{20}$R$^{21}$; aryl; heterocycle; —OalkylOC(=O)R$^{18}$; C(=O)N(C$_{1-6}$ alkyl), N(H)S(O)(O)(C$_{1-6}$ alkyl); arylalkyloxy; aryloxy; arylalkyloxy; or arylalkyl; each of which is unsubstituted or substituted with 1 or more =O; NR$^{20}$R$^{21}$; CN; alkoxy; heterocycle; haloalkyl- or alkyl-substituted heterocycle; heterocycle linked to R$^{17}$ by alkyl; alkoxyalkoxy or halogen. R$^{18}$ as a substituent here is generally not H. R$^{19}$ typically is independently halogen, N(R$^{20}$R$^{21}$), alkoxy or halo-substituted alkyl or alkoxy. R$^{19}$ usually is positioned para and/or ortho to the carbon bound to R$^{17}$.

R$^{26}$ is typically cyclopentyl, cyclohexyl or hydrogen.

Substituents optionally are depicted with or without bonds. Regardless of bond indications, if a substituent is polyvalent (based on its position in the structure referred to), then any and all possible orientations of the substituent are intended.

Haloalkyl or haloalkyloxy typically are —CF$_3$ or —OCF$_3$.

Formula (A) depicts optional single or double bonds. It will be understood that the bonds are present such that the aromatic nature of the nucleus of formula (A) is preserved, i.e., these formulae are intended to embrace all possible tautomers.

It will be understood that when applicants refer to a particular substituent site as "general", "typical" or "usual" (or otherwise designate a subselection of group(s) for a given substituent site), this is to be construed as expressly teaching individual compound(s) or compound subgenera in which the selected site(s) possesses the recited feature(s) while the remaining substituent sites retain the full options set forth above for formula (A). The subselections are to be considered to disclose expressly all compounds having the subselections in combination or subcombination, alone and/or taken together with the full scope of remaining substituents described above for formula (A). For instance, disclosure of the substituent X and Y subselections above is disclosure of (a) a subgenus in which X is methylene, Y is a bond and the other groups are set forth in formula (A), (b) a subgenus in which X is methylene and all the other groups (including Y) are set forth in formula (A) and (c) a subgenus in which Y is a bond and all the other groups (including X) are as set forth in formula (A). As another example, the recitations above regarding R$^3$ shall be construed as teaching at least compounds of formula (A) in which all groups other than R$^3$ are as set forth above in formula (A) and R$^3$ is aryl substituted with 1 R$^{17}$, 2 R$^{17}$ or 3 R$^{17}$, any of these substituted with any of 1, 2 or 3 R$^{19}$ groups, and the same options for heterocycles or any of the specified subclasses or specific heterocycles. This convention is adopted to provide support for subgenera without burdening this application with redundant and/or unduly lengthy recitations of background groups common to various subgenera.

The term "prodrug" as used herein refers to any compound that when administered to a biological system generates the drug substance, i.e. active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically-active compound.

Prodrugs

Certain of the compounds herein when substituted with appropriate selected functionalities are capable of acting as prodriags. These are labile functional groups which separate from an active inhibitory compound during metabolism, systemically, inside a cell, by hydrolysis, enzymatic cleavage, or by some other process (Bundgaard, Hans, "Design and Application of Prodrugs" in Textbook of Drug Design and Development (1991), P. Krogsgaard-Larsen and H. Bundgaard, Eds. Harwood Academic Publishers, pp. 113-191). These prodrug moieties can serve to enhance solubility, absorption and lipophilicity to optimize drug delivery, bioavailability and efficacy. A "prodrug" is thus a covalently modified analog of a therapeutically-active compound. A prodrug moiety of course can be therapeutically active in its own right.

Exemplary prodrug moieties include the hydrolytically sensitive or labile esters (—CO$_2$R') of carboxylic acids (—CO$_2$H) or other functional groups with an acidic proton which is bound to the imidazo[4,5-c]pyridine compounds of the invention. The R' group of such hydrolytically sensitive or labile esters may include: (i) acyloxymethyl esters —CH$_2$OC(O)R$^{9a}$; and (ii) acyloxymethyl carbonates —CH$_2$C(=O)OR$^{9a}$ where R$^{9a}$ is C$_1$-C$_6$ alkyl, C$_1$-C$_6$ substituted alkyl, C$_6$-C$_{20}$ aryl or C$_6$-C$_{20}$ substituted aryl. A close variant of the acyloxyalkyl ester, the alkoxycarbonyloxyalkyl ester (carbonate), may also enhance oral bioavailability as a prodrug moiety in the compounds of the invention. An exemplary acyloxymethyl ester R group is pivaloyloxymethoxy, (POM) —CH$_2$C(=O)C(CH$_3$)$_3$. An exemplary acyloxymethyl carbonate prodrug moiety is pivaloyloxymethylcarbonate (POC)—CH$_2$C(=O)OC(CH$_3$)$_3$. Cleavable moieties capable of acting as prodrug functionalities are optionally linked at any tolerant site on the compound of this invention, for example R$^3$ and any of its substituents.

Utilities

The compounds of this invention, or the metabolites produced from these compounds In vivo, have a large number of uses. They are useful in immunology, chromatography, diagnostics and therapeutics, among other fields.

The compounds of formula (A) are conjugated to immunogenic polypeptides as a reagent for eliciting antibodies capable of binding specifically to the polypeptide, to the compounds or to their metabolic products which retain immunologically recognized epitopes (sites of antibody binding). These immunogenic compositions therefore are useful as intermediates in the preparation of antibodies for use in diagnostics, quality control, or the like, or in assays for the compounds of formula (A) or their novel metabolic products. The compounds are useful for raising antibodies against otherwise non-immunogenic polypeptides, in that the compounds serve as haptenic sites stimulating an immune response which cross-reacts with the unmodified conjugated protein.

Conjugates of the compounds of formula (A) with immunogenic polypeptides such as albumin or keyhole limpet hemocyanin generally are useful as immunogens. The polypeptides are conjugated at the same sites denoted for amino acids. The metabolic products described above may retain a substantial degree of immunological cross reactivity with the compounds of the invention. Thus, the antibodies of this invention will be capable of binding to the unprotected compounds of the invention without binding to the protected compounds. Alternatively the metabolic products will be capable of binding to the protected compounds and/or the metabolitic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results.

The immunogens of this invention contain the compound of this invention presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se, and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or alkN=C=Nalk are useful in preparing the conjugates of this invention. The conjugates comprise a compound of the invention attached by a bond or a linking group of 1-100, typically, 1-25, more typically 1-10 carbon atoms to the immunogenic substance. The conjugates are separated from starting materials and by products using chromatography or the like, and then are sterile filtered and vialed for storage.

Animals are typically immunized against the immunogenic conjugates or derivatives and antisera or monoclonal antibodies prepared in conventional fashion.

The compounds of this invention are useful as linkers, spacers or affinity (typically hydrophobic) moieties in preparing affinity absorption matrices. The compounds of the invention optionally are bound covalently to an insoluble matrix and used for affinity chromatography separations, depending on the nature of the groups of the compounds, for example compounds with pendant aryl groups are useful in making hydrophobic affinity columns.

They also are useful as linkers and spacers in preparing immobilized enzymes for process control, or in making immunoassay reagents. The compounds herein contain functional groups that are suitable as sites for cross-linking desired substances. For example, it is conventional to link affinity reagents such as hormones, peptides, antibodies, drugs, and the like to insoluble substrates. These insolublized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

The compounds of this invention are labeled with detectable moieties such biotin, radioisotopes, enzymes and the like for diagnostic purposes. Suitable techniques for accomplishing the labeling of the compounds of formula (A) are well known and will be apparent to the artisan from consideration of this specification as a whole. For example, one suitable site for labeling is $R^{17}$ or $R^{19}$.

More typically, however, the compounds of the invention are employed for the treatment or prophylaxis of viral infections such as yellow fever virus, Dengue virus, hepatitis B virus, hepatitis G virus, Classical Swine Fever virus or the Border Disease Virus, but more particularly flaviviral or picornaviral infections, in particular, HCV and BVDV.

The therapeutic compound(s) of this invention are administered to a subject mammal (including a human) by any means well known in the art, i.e. orally, intranasally, subcutaneously, intramuscularly, intradermally, intravenously, intra-aiterially, parenterally or by catheterization. The therapeutically effective amount of the compound(s) is a flaviviral or picornaviral growth inhibiting amount. More preferably, it is a flaviviral or picornaviral replication inhibiting amount or a flaviviral or picornaviral enzyme inhibiting amount of the compounds of formula (A). This is believed to correspond to an amount which ensures a plasma level of between about 1 μg/ml and 100 mg/ml, optionally of 10 mg/ml. This optionally is achieved by administration of a dosage of in the range of 0.001 mg to 60 mg, preferably 0.01 mg to 10 mg, preferably 0.1 mg to 1 mg per day per kg bodyweight for humans. These are starting points for determining the optimal dosage of the compound of this invention. The actual amount will depend upon many factors known to the artisan, including bioavailability of the compound, whether it contains a prodrug functionality, its metabolism and distribution in the subject and its potency, among others. It typically is necessary to determine the proper dosing in the clinical setting, and this is well within the skill of the ordinary artisan. The therapeutically effective amount of the compound(s) of this invention optionally are divided into several sub-units per day or are administered at daily or more than one day intervals, depending upon the pathologic condition to be treated, the patient's condition and the nature of the compound of this invention.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27 or tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration.

Suitable anti-viral agents for inclusion in combination antiviral compositions or for coadministration in a course of therapy with the compounds of this invention include, for instance, interferon alpha, ribavirin, a compound falling within the scope of disclosure of EP1162196, WO 03/010141, WO 03/007945 and WO 03/010140, a compound falling within the scope of disclosure of WO 00/204425, and other patents or patent applications within their patent families, in amounts of 1 to 99.90% by weight compound of this invention, preferably from 1 to 99% by weight, more preferably from 5 to 95% by weight as can be readily determined by one skilled in the art. Such co-administered agents need not be formulated in the same dosage form as the compound of the invention. They optionally are simply administered to the subject in the course of treatment along with a course of treatment with a compound of formula (A).

The present invention further provides veterinary compositions comprising at least one active ingredient as above defined together with a veterinary carrier therefore, for example in the treatment of BVDV. Veterinary carriers are materials useful for the purpose of administering the composition and are excipients which are otherwise inert or acceptable in the veterinary art and are compatible with the compound of this invention. These veterinary compositions may be administered orally, parenterally or by any other desired route.

Salts

The term "pharmaceutically acceptable salts" as used herein means the therapeutically active non-toxic salt forms formed by the compounds of formula (A). Such salts may include those derived by combination of appropriate cations such as alkali and alkaline earth metal ions or ammonium and quaternary amino ions with an acid anion moiety, typically a carboxylic acid.

The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions).

Metal salts typically are prepared by reacting the metal hydroxide with a compound of this invention. Examples of metal salts which are prepared in this way are salts containing Li+, Na+, Ca+2 and Mg+2 and K+. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, benzoic, 2-hydroxypropanoic, 2-oxopropanoic, lactic, fumaric, tartaric, pyruvic, maleic, malonic, malic, salicylic (i.e. 2-hydroxybenzoic), p-aminosalicylic, isethionic, lactobionic, succinic oxalic and citric acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids, C1-C6 allylsulfonic, benzenesulfonic, p-toluenesulfonic, cyclohexanesulfamic, and the like. Preferred salts include mesylate and HCl.

The compounds of this invention include the solvates formed with the compounds of formula (A) and their salts, such as for example hydrates, alcoholates and the like. The compositions herein comprise compounds of the invention in their un-ionized, as well as zwitterionic form, and combinations with stoichiometric amounts of water as in hydrates.

Also included within the scope of this invention are the salts of the compounds of formula (A) with one or more amino acids as described above. The amino acid typically is one bearing a side chain with a basic or acidic group, e.g., lysine, arginine or glutamic acid, or a neutral group such as glycine, serine, threonine, alanine, isoleucine, or leucine.

Salts of acids or bases which are not physiologically acceptable may also find use, for example, in the preparation or purification of a compound of formula (A). All salts, whether or not derived form a physiologically acceptable acid or base, are within the scope of the present invention.

Isomers

The term "isomers" as used herein means all possible isomeric forms, including tautomeric and stereochemical forms, which the compounds of formula (A) may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formula (A) may have one or more chiral centers), as well as the stereochemically pure or enriched isomers. More particularly, stereogenic centers may have either the R- or S-configuration, and double or triple bonds optionally are in either the cis- or trans-configuration.

Enriched isomeric forms of a compound of this invention are defined as a single isomer substantially free of the compound's other enantiomers or diastereomers. In particular, the term "stereoisomerically enriched" or "chirally enriched" relates to compounds having a single stereoisomeric proportion of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" contain undetectable levels of any other isomer.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Locbmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing an acidic functionality, such as carboxylic acid and sulfonic acid.

The diastereomeric salts optionally are induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994). Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using, a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990). "Optical resolution of dihydropyridine enantiomers by High-performance liquid chromatography using phenylcarbamates of polysaccharides as a chiral stationary phase", J. of Chromatogr. 513:375-378).

Metabolites

The present invention also provides the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. C14 or H3) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no antiviral activity of their own.

Formulations

The compounds of the invention optionally are formulated with conventional pharmaceutical carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents, may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylaiylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with polypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of as active ingredient one or more compounds of the invention ("controlled release formulationss") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

EXAMPLES

The following examples illustrate the present invention without being limited thereto. Part A represents the preparation of the compounds whereas Part B represents the pharmacological examples and Part C represents biological activities of selected compounds of the invention.

Part A

Preparation of 2-(2-Fluoro-phenyl)-6-(4-trifluoromethoxy-benzyl)-6H-pyrrolo[2,3-c]pyridine

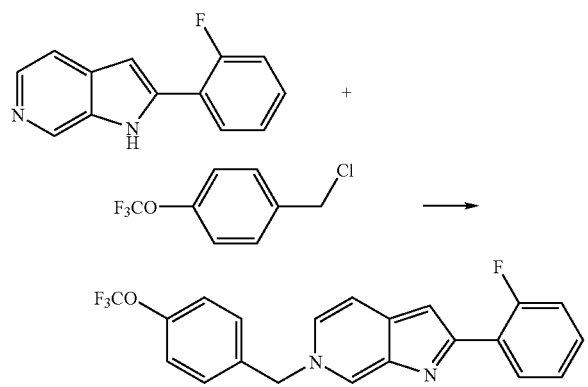

To a solution of 2-(2-Fluoro-phenyl)-1H-pyrrolo[2,3-c]pyridine (50 mg, 0.244 mmole) in DMF (1 ml) was added 10% (w/v) aqueous NaOH (113 µl, 0.28 mmole) followed by a solution of 4-trifluoromethoxybenzoyl chloride (60 mg, 0.28 mmole) in DMF (0.5 ml). The reaction mixture was stirred at room temperature for 1 hour. The crude reaction mixture was purified by reverse phase HPLC with mass directed collection. Obtained 9.2 mg (8%) of 2-(2-Fluoro phenyl)-6-(4-trifluoromethoxy-benzyl)-6H-pyrrolo[2,3-c]pyridinium trifluoroacetate after repurification.

Preparation of 2-(2-Fluoro-phenyl)-5-(4-trifluoromethoxy-benzyl)-5H-pyrrolo[3,2-c]pyridine

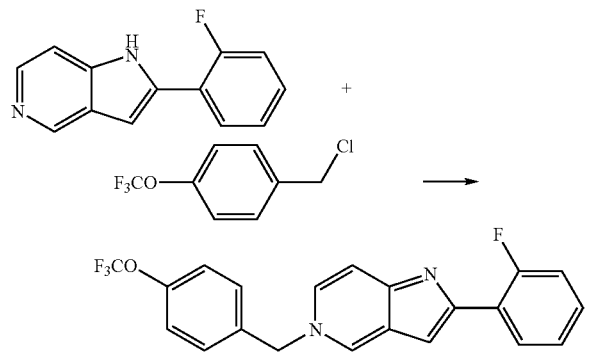

To a solution of 2-(2-Fluoro-phenyl)-1H-pyrrolo[3,2-c]pyridine (50 mg, 0.244 mmole) in DMF (1 ml) was added 10% (w/v) aqueous NaOH (113 µl, 0.28 mmole) followed by a solution of 4-trifluoromethoxybenzoyl chloride (60 mg, 0.28 mmole) in DMF (0.5 ml). The reaction mixture was stirred at room temperature for 1 hour. The crude reaction mixture was purified by reverse phase HPLC with mass directed collection. Obtained 87 mg (74%) of 2-(2-Fluoro-phenyl)-5-(4-trifluoromethoxy-benzyl)-5H-pyrrolo[3,2-c]pyridinium trifluoroacetate.

Preparation of 2-(2-Fluoro-phenyl)-6-[3-(4-fluoro-2-trifluoromethyl-phenyl)-isoxazol-5-ylmethyl]-6H-pyrrolo[2,3-c]pyridine trifluoroacetate

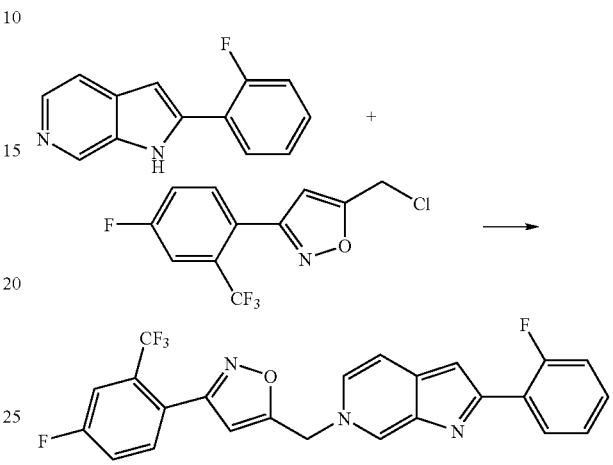

To a solution of 2-(2-Fluoro-phenyl)-1H-pyrrolo[2,3-c]pyridine (50 mg, 0.244 mmole) in DMF (1 ml) was added 10% (w/v) aqueous NaOH (113 µl, 0.28 mmole) followed by a solution of 5-Chloromethyl-3-(4-fluoro-2-trifluoromethyl-phenyl)-isoxazole (79 mg, 0.28 mmole) in DMF (0.5 ml). The reaction mixture was stirred at room temperature for 12 hours. The crude reaction mixture was purified by reverse phase HPLC with mass directed collection. Obtained 109 mg (81%) of 2-(2-Fluoro-phenyl)-6-[3-(4-fluoro-2-trifluoromethyl-phenyl)-isoxazol-5-ylmethyl]-6H-pyrrolo[2,3-c]pyridinium trifluoroacetate.

Preparation of 2-(2-Fluoro-phenyl)-5-[3-(4-fluoro-2-trifluoromethyl-phenyl)-isoxazol-5-ylmethyl]-5H-pyrrolo[3,2-c]pyridine trifluoroacetate

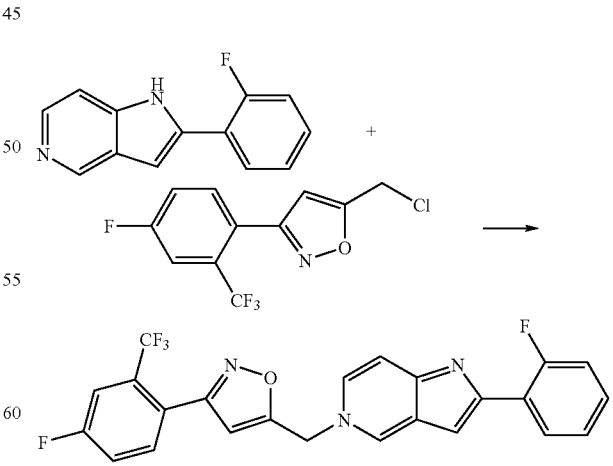

To a solution of 2-(2-Fluoro-phenyl)-1H-pyrrolo[3,2-c]pyridine (50 mg, 0.244 mmole) in DMF (1 ml) was added 10% (w/v) aqueous NaOH (113 µL, 0.28 mmole) followed by a solution of 5-Chloromethyl-3-(4-fluoro-2-trifluoromethylphenyl)-isoxazole (79 mg, 0.28 mmole) in DMF (0.5 ml). The reaction mixture was stirred at room temperature for 12 hours. The crude reaction mixture was purified by reverse phase HPLC with mass directed collection. Obtained 115 mg (86%) of 2-(2-Fluoro-phenyl)-5-[3-(4-fluoro-2-trifluoromethyl-phenyl)-isoxazol-5-ylmethyl]-5H-pyrrolo[3,2-c]pyridinium trifluoroacetate.

Preparation of 3-cyclohexyl-6-((3-(4-fluoro-2-(trifluoromethyl)isoxazol-5-yl)methyl)-2-phenyl-6H-pyrrolo[2,3-c]pyridine

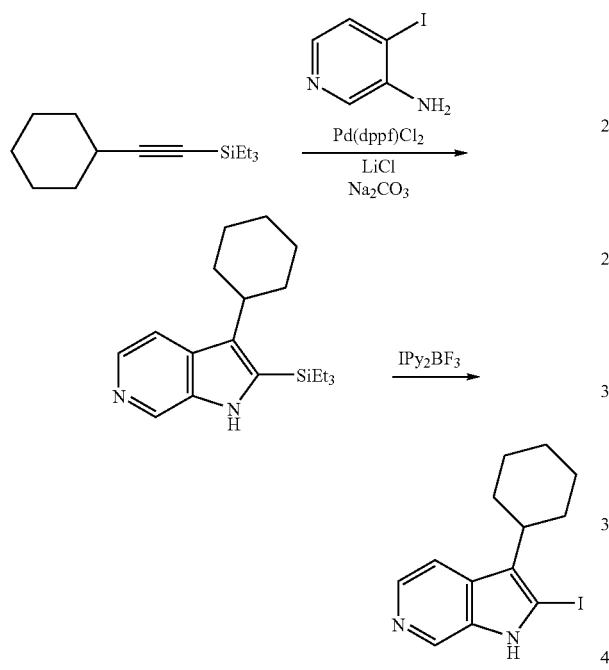

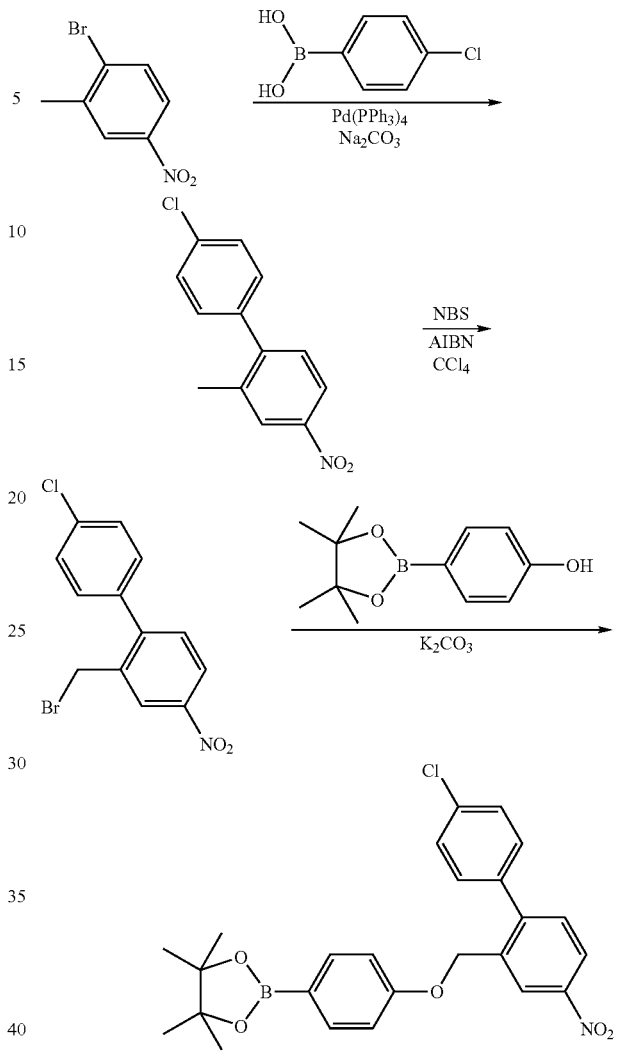

To triethylsilylcyclohexylacetylene (1.36 g, 6.20 mmol) synthesized as described in Tet. Lett. 41: 907 (2000) and 4-iodo-pyridin-3-ylamine (1.62 g, 2.27 mmol) in anhydrous DMF (62 mL) was added Pd(dppf)Cl$_2$-CH$_2$Cl$_2$ (253 mg, 0.31 mmol) followed by anhydrous LiCl (263 mg, 6.20 mmol) and Na$_2$CO$_3$ (1.31 g, 12.40 mmol). The reaction mixture was heated to 100° C. for 24 h after which the reaction was diluted with H$_2$O and EtOAc and filtered over celite. The organics were separated, washed with saturated aqueous NaHCO$_3$, and dried over sodium sulfate. After removal of solvent, the crude product was purified by column chromatography on silica (3:2 ethyl acetate/hexanes) to provide 590 mgs (30%) of desired product.

Bis(pyridine)iodonium tetrafluoroborate (250 mg, 0.67 mmol) was dissolved in anhydrous CH$_2$Cl$_2$ (4 mL). To this solution was added a solution of 2-(triethylsilyl)pyrrolopyridine (192 mg, 0.61 mmol) in CH$_2$Cl$_2$ (2.7 mL) followed by trific acid (183 mg, 1.22 mmol). After stirring for 1.5 h at room temperature, the reaction was diluted with H$_2$O and the organics were separated. The organic layer was washed with a 10% solution of aqueous Na$_2$S$_2$O$_3$, dried over sodium sulfate, and removed via rotary evaporation. The crude material (100 mg, 50%) was used without further purification: LCMS found 327.2 (M$^+$+H, C$_{13}$H$_{15}$IN$_2$ requires 327.2).

To 2-bromo-5-nitrotoluene (500 mg, 2.31 mmol) and 4-chlorophenylboronic acid (626 mg, 4.00 mmol) in DMF (15 mL) was added a solution of Na$_2$CO$_3$ (695 mg, 6.56 mmol) in H$_2$O (8 mL) followed by the addition of Pd(PPh$_3$)$_4$ (125 mg, 5 mol %). The reaction was heated in a microwave reactor at 200° C. for 3 min. The reaction mixture was filtered over celite and solvents removed under reduced pressure. The crude product was purified by column chromatography on silica (2:1 hexanes/ethyl acetate) to provide 483 mg (84%) of desired product.

2-(4-Chlorophenyl)-5-nitrotoluene (483 mg, 1.95 mmol) and NBS (382 mg, 2.15 mmol) were combined in CCl$_4$ (13 mL). After heating to 88° C., AIBN (32 mg, 0.2 mmol) was added and reacted for 20 h. The reaction was cooled to room temperature and diluted with CH$_2$Cl$_2$ and H$_2$O. The organics were separated, washed with saturated aqueous NaHCO$_3$, and dried over sodium sulfate. After removal of solvent, the crude material was used directly in the next reaction.

To α-bromo-2-(4-chlorophenyl)-5-nitrotoluene (297 mg, 0.91 mmol) 4-(4,4,5,5-tetramethyl-1,3,2-dioxaborolan-2-yl) phenol (167 mg, 0.76 mmol) in DMF (3 mL) was added K$_2$CO$_3$ (209 mg, 1.51 mmol). After stirring for 2 h at room temperature, the reaction was diluted with H$_2$O and extracted with EtOAc. The organics were separated, washed with saturated aqueous NaHCO$_3$, and dried over sodium sulfate. After removal of solvent, the crude product was purified by column chromatography on silica (9:1 hexanes/ethyl acetate) to provide 160 mg (45%) of desired product: $^1$H NMR (CDCl$_3$, 300 MHz) δ 8.54 (d, 1H), 8.25 (dd, 1H), 7.74 (d, 2H), 7.27-7.49 (m, 5H), 6.86 (d, 2H), 4.98 (s, 2H), 1.34 (s, 12H).

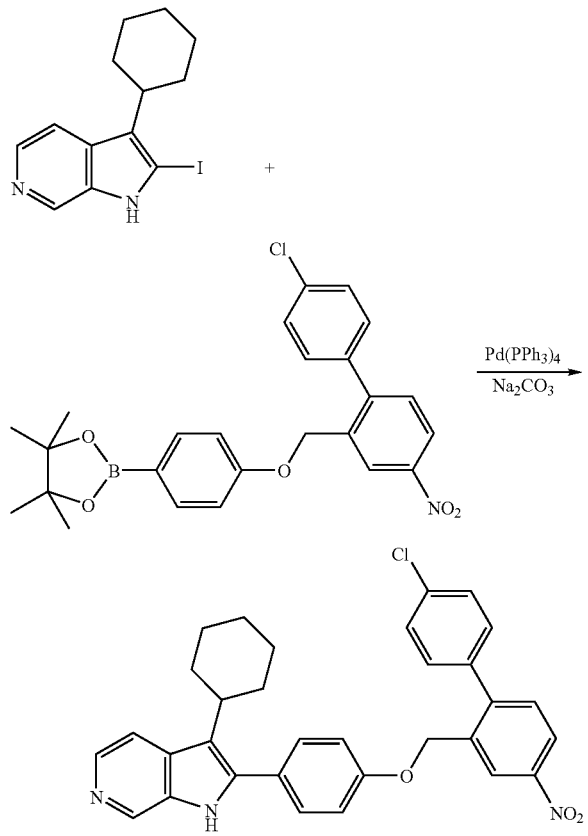

To 3-cyclohexyl-2-iodo-1H-pyrrolo[2,3-c]pyridine (34 mg, 0.1 mmol) and substituted boronic ester (58 mg, 0.13 mmol) in DMF (0.69 mL) was added a solution of Na$_2$CO$_3$ (33 mg, 0.31 mmol) in H$_2$O (0.35 mL) followed by Pd(PPh$_3$)$_4$ (6 mg, 5 mol %). The reaction mixture was heated to 90° C. for 12 h after which the reaction was filtered over a C-18 SPE column flushing with MeOH. After removal of solvent, the crude product was purified by column chromatography on silica (3% MeOH in CH$_2$Cl$_2$) to provide 6.1 mg (11%) of the title compound: $^1$H NMR (CD$_3$OD, 300 MHz) δ 8.79 (s, 1H), 8.54 (d, 1H), 8.31 (dd, 1H), 8.11 (q, 2H), 7.49-7.63 (m, 7H), 7.12 (d, 2H), 5.16 (s, 2H), 3.00 (m, 1H), 1.78-2.02 (m, 7H), 1.42 (m, 3H); LCMS found 538.4 (M$^+$+H, C$_{32}$H$_{28}$ClN$_3$O$_3$ requires 539.0).

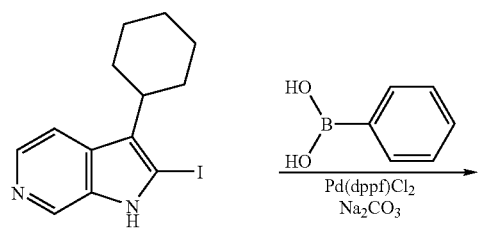

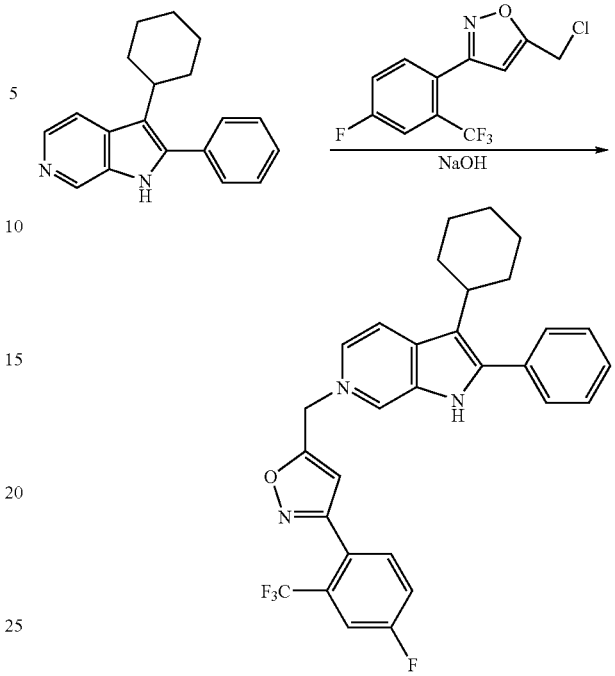

To 3-cyclohexyl-2-iodo-1H-pyrrolo[2,3-c]pyridine (70 mg, 0.22 mmol) and phenylboronic acid (31 mg, 0.26 mmol) in toluene/EtOH (1:1, 1.76 mL) was added a solution of Na$_2$CO$_3$ (68 mg, 0.65 mmol) in H$_2$O (0.44 mL) followed by Pd(dppf)Cl$_2$·CH$_2$Cl$_2$ (8.8 mg, 5 mol %). The reaction mixture was heated to 90° C. for 12 h after which the reaction was filtered over a C-18 SPE column flushing with MeOH. After removal of solvent, the crude product was purified by column chromatography on silica (4% MeOH in CH$_2$Cl$_2$) to provide 30 mg (83%) of desired product: $^1$H NMR CD$_3$OD, 300 MHz) δ 8.70 (s, 1H), 8.06 (d, 1H), 7.92 (dd, 1H), 7.50-7.60 (m, 5H), 2.98 (m, 1H), 1.78-2.06 (m, 7H), 1.30-1.47 (m, 3H); LCMS found 277.5 (M$^+$+H, C$_{19}$H$_{20}$N$_2$ requires 277.4).

To 3-cyclohexyl-2-phenyl-1H-pyrrolo[2,3-c]pyridine (9 mg, 33 µmol) and 5-(chloromethyl)-3-(4-fluoro-2-(trifluoromethyl)phenyl)isoxazole (11 mg, 39 µmol) in DMF (326 µL) was added 10% aqueous NaOH (16 mL, 39 µmol). After stirring 12 h at room temperature, the reaction was neutralized with triethylamine and the crude purified by reverse phase HPLC to provide 4.5 mg (27%) of the title compound: $^1$H NMR (CD$_3$OD, 300 MHz) δ 9.2 (s, 1H), 8.36 (s, 2H), 7.55-7.72 (m, 8H), 6.82 (s, 1H), 6.12 (s, 2H), 3.04 (m, 1H), 1.78-2.06 (m, 7H), 1.30-1.50 (m, 3H); LCMS found 520.3 (M$^+$+H, C$_{30}$H$_{26}$F$_4$N$_3$O requires 520.5).

Part B

Methodology for Determination of Antiviral and Cytostatic Activity

Anti-HCV Assay/Replicon Assay

Huh-5-2 cells [a cell line with a persistent HCV replicon I389luc-ubi-neo/NS3-3'/5.1; replicon with firefly luciferase-ubiquitin-neomycin phosphotransferase fusion protein and EMCV-IRES driven NS3-5B HCV polyprotein] was cultured in RPMI medium (Gibco) supplemented with 10% fetal calf serum, 2 mM L-glutamine (Life Technologies), 1× non-essential amino acids (Life Technologies); 100 IU/ml penicillin and 100 ug/ml streptomycin and 250 ug/ml G418 (Geneticin, Life Technologies). Cells were seeded at a density of 7000 cells per well in 96 well View Plate™ (Packard) in medium containing the same components as described above, except for G418. Cells were allowed to adhere and proliferate for 24 hr. At that time, culture medium was removed and serial dilutions of the test compounds were added in culture medium lacking G418. Interferon alfa 2a (500 IU) was included as a positive control. Plates were further incubated at 37° C. and 5% $CO_2$ for 72 hours. Replication of the HCV replicon in Huh-5 cells results in luciferase activity in the cells. Luciferase activity is measured by adding 50 µl of 1× Glo-lysis buffer (Promega) for 15 minutes followed by 50 µL of the Steady-Glo Luciferase assay reagent (Promega). Luciferase activity is measured with a luminometer and the signal in each individual well is expressed as a percentage of the untreated cultures. Parallel cultures of Huh-5-2 cells, seeded at a density of 7000 cells/well of classical 96-well cel culture plates (Becton-Dickinson) are treated in a similar fashion except that no Glo-lysis buffer or Steady-Glo Luciferase reagent is added. Instead the density of the culture is measured by means of the MTS method (Promega).

Quantitative Analysis of HCV RNA by Taqman Real-Time RT-PCR

Replicon cells were plated at $7.5 \times 10^3$ cells per well in a 96-well plate plates at 37° C. and 5% $CO_2$ in Dulbecco's modified essential medium containing 10% fetal calf serum, 1% nonessential amino acids and 1 mg/ml Geneticin. After allowing 24 h for cell attachment, different dilutions of compound were added to the cultures. Plates were incubated for 5 days, at which time RNA was extracted using the Qiamp Rneazyi Kit (Qiagen, Hilden, Germany). A 50 µL PCR reaction contained TaqMan EZ buffer (50 mmol/L Bicine, 115 mmol/L potassium acetate, 0.01 mmol/L EDTA, 60 nmol/L 6-carboxy-X-rhodamine, and 8% glycerol, pH 8.2; Perkin Elmer Corp./Applied Biosystems), 300 µmol/L deoxyadenosine triphosphate, 300 µmol/L deoxyguanosine triphosphate, 300 µmol/L deoxycytidine triphosphate, 600 µmol/L deoxyuridine triphosphate, 200 µmol/L forward primer [5'-ccg gcT Acc Tgc ccA TTc], 200 µmol/L reverse primer [ccA GaT cAT ccT gAT cgA cAA G], 100 µmol/L TaqMan probe [6-FAM-AcA Tcg cAT cgA gcg Agc Acg TAc-TAMRA], 3 mmol/L manganese acetate, 0.5 U AmpErase uracil-N-glycosylase, 7.5 U rTth DNA polymerase, and 10 µl of RNA elution. After initial activation of uracil-N-glycosylase at 50° C. for 2 minutes, RT was performed at 60° C. for 30 minutes, followed by inactivation of uracil-N-glycosylase at 95° C. for 5 minutes. Subsequent PCR amplification consisted of 40 cycles of denaturation at 94° C. for 20 seconds and annealing and extension at 62° C. for 1 minute in an ABI 7700 sequence detector. For each PCR run, negative template and positive template samples were used. The cycle threshold value (Ct-value) is defined as the number of PCR cycles for which the signal exceeds the baseline, which defines a positive value. The sample was considered to be positive if the Ct-value was <50. Results are expressed as genomic equivalents (GE).

Part C

Biological Activities of Selected Compounds

Representative compounds of the invention are shown in Table 1. The compounds shown were active, with HCV replicon $EC_{50}$ values less than 100 uM.

TABLE 1

| Compound | Structure |
|---|---|
| 1 | 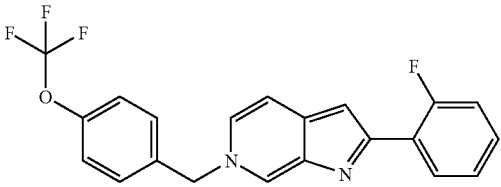 |
| 2 | 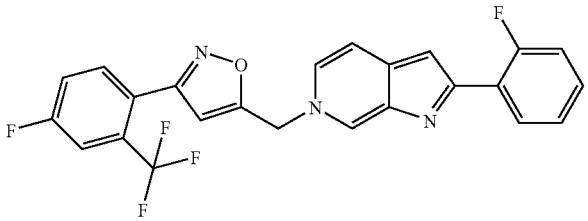 |

TABLE 1-continued
| Compound | Structure |
|---|---|
| 3 | 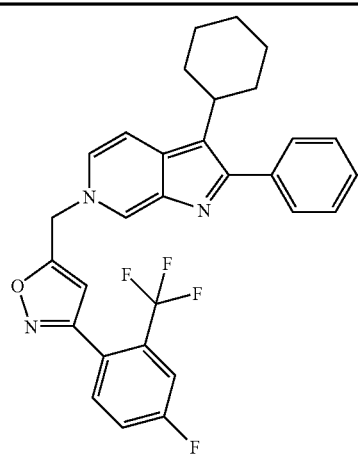 |
| 4 | 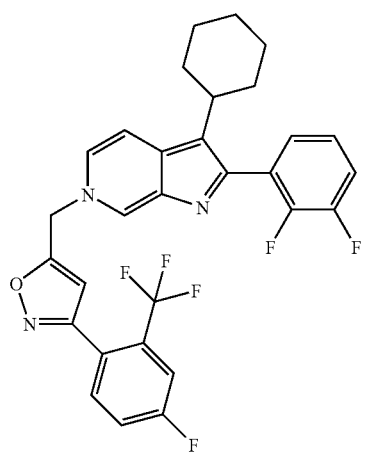 |
| 5 | 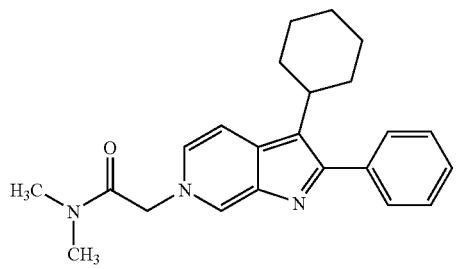 |
| 6 | 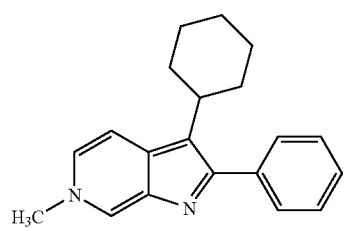 |

TABLE 1-continued

| Compound | Structure |
|---|---|
| 7 | 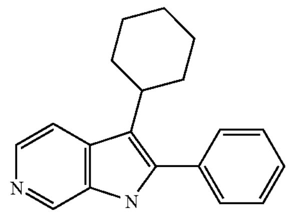 |
| 8 | 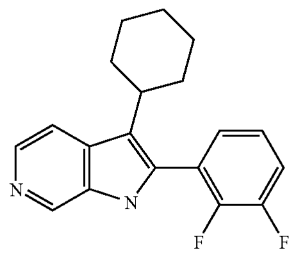 |
| 9 | 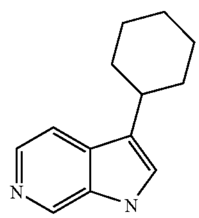 |
| 10 | 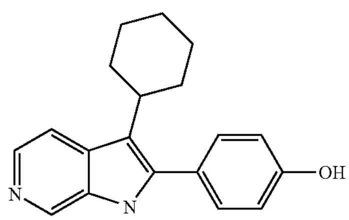 |
| 11 | 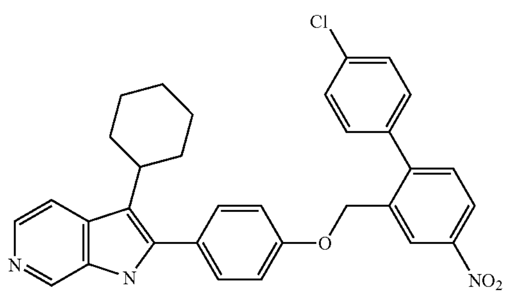 |
| 12 | 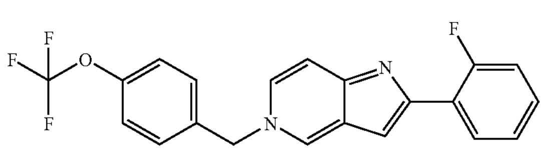 |
| 13 | 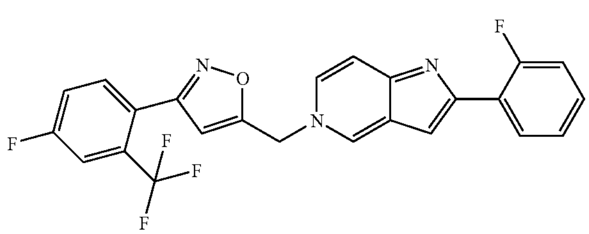 |

TABLE 1-continued

| Compound | Structure |
|---|---|
| 14 | 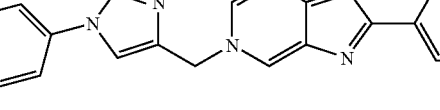 |
| 15 | 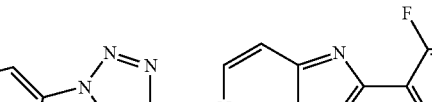 |
| 16 | 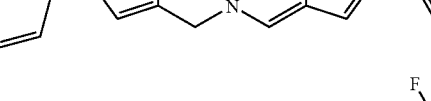 |
| 17 | 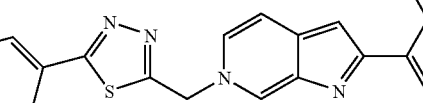 |
| 18 | 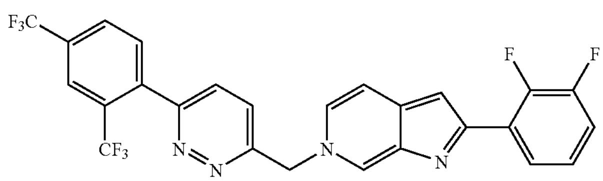 |
| 19 | 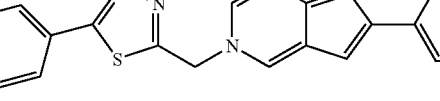 |

We claim:

1. A compound having the general formula (A),

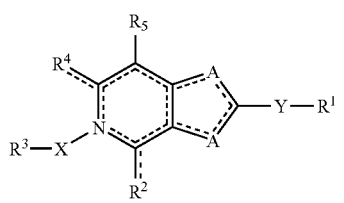

wherein:
the dotted lines represent at least 3, optionally 4 double bonds, provided that no two double bonds are adjacent to one another;

A is —N= and the other one A is $CR^{26}$;

$R^1$ is selected from hydrogen, aryl, heterocycle, $C_1$-$C_{10}$ alkoxy, thioalkyl, $C_1$-$C_{10}$ alkyl-amino, $C_1$-$C_{10}$ dialkyl-amino, $C_{3-10}$ cycloalkyl, $C_{4-10}$ cycloalkenyl, and $C_{4-10}$ cycloalkynyl, wherein each are optionally substituted with 1 or more $R^6$;

Y is selected from a single bond, O, S(O)$_m$, $NR^{10}$, alkylene, $C_{2-10}$ alkenylene, or $C_{2-10}$ alkynylene, wherein 1 to 3 -C(H)=, —C(=) or —CH$_2$— groups of each alkylene, alkenylene or alkynylene optionally are independently replaced with a heteroatom or heteroatom group selected from —O—, =O, —OR$^{27}$, —S—, =S, —SR$^{27}$, —NR$^{27}$, —N(R$^{27}$)$_2$, where $R^{27}$ independently is hydrogen, $C_{1-18}$ alkyl, $C_{2-18}$ alkenyl, or $C_{2-18}$ alkynyl; provided that $YR^1$ is not hydrogen or $C_{1-6}$ alkyl;

$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{3-10}$ cycloalkynyl, or heterocycle;

X is absent or is selected from hydrogen, alkylene, $C_{2-10}$ alkenylene or $C_{2-10}$ alkynylene, wherein 1 to 3

—C(H)=, —C(≡) or —CH$_2$— groups of each alkylene, alkenylene or alkynylene optionally are independently replaced with a heteroatom or heteroatom group selected from —O—, =O, —OR$^{27}$, —S—, =S, —SR$^{27}$, —NR$^{27}$, —N(R$^{27}$)$_2$, where R$^{27}$ independently is hydrogen, C$_{1-18}$ alkyl, C$_{2-18}$ alkenyl, or C$_{2-18}$ alkynyl; m is any integer from 0 to 2;

R$^3$ is absent or is selected from hydrogen, aryl, aryloxy, arylthio, cycloalkyl, cycloalkenyl, cycloalkynyl, aryl-N(R$^{10}$)—, or an aromatic heterocycle, where each said substituent is optionally substituted with 1 or more R$^{17}$, provided that for cycloalkenyl the double bond is not adjacent to a nitrogen;

R$^5$ is selected from hydrogen, C$_{1-18}$ alkyl, C$_{2-18}$ alkenyl, C$_{2-18}$ alkynyl, C$_{1-18}$ alkoxy, C$_{1-18}$ alkylthio, halogen, —OH, —CN, —NO$_2$, —NR$^7$R$^8$, haloalkyloxy, haloalkyl, —C(=O)R$^9$, —C(=O)OR$^9$, —C(=S)R$^9$, SH, aryl, aryloxy, arylthio, arylalkyl, C$_{1-18}$ hydroxyalkyl, C$_{3-10}$ cycloalkyl, C$_{3-10}$ cycloalkyloxy, C$_{3-10}$ cycloalkylthio, C$_{3-10}$ cycloalkenyl, C$_{7-10}$ cycloalkynyl, or heterocycle;

R$^6$ is selected from hydrogen, C$_{1-18}$ alkyl, C$_{2-18}$ alkenyl, C$_{2-18}$ alkynyl, C$_{1-18}$ alkoxy, C$_{1-18}$ alkylthio, C$_{1-18}$ alkylsulfoxide, C$_{1-18}$ alkylsulfone, C$_{1-18}$ halo-alkyl, C$_{2-18}$ halo-alkenyl, C$_{2-18}$ halo-alkynyl, C$_{1-18}$ halo-alkoxy, C$_{1-18}$ halo-alkylthio, C$_{3-10}$ cycloalkyl, C$_{3-10}$ cycloalkenyl, C$_{7-10}$ cycloalkynyl, halogen, OH, CN, cyanoalkyl, —CO$_2$R$^{18}$, NO$_2$, —NR$^7$R$^8$, C$_{1-18}$ haloalkyl, C(=O)R$^{18}$, C(=S)R$^{18}$, SH, aryl, aryloxy, arylthio, arylsulfoxide, arylsulfone, arylsulfonamide, aryl(C$_{1-18}$)alkyl, aryl(C$_{1-18}$)alkyloxy, aryl(C$_{1-18}$)alkylthio, heterocycle and C$_{1-18}$ hydroxyalkyl, where each is optionally substituted with 1 to 3 R$^{19}$;

R$^7$ and R$^8$ are independently selected from hydrogen, C$_{1-18}$ alkyl, C$_{1-18}$ alkenyl, aryl, C$_{3-10}$ cycloalkyl, C$_{4-10}$ cycloalkenyl, heterocycle, —C(=O)R$^{12}$; —C(=S)R$^{12}$, an amino acid residue linked through a carboxyl group thereof, or R$^7$ and R$^8$ are taken together with the nitrogen to form a heterocycle;

R$^9$ and R$^{18}$ are independently selected from hydrogen, OH, C$_{1-18}$ alkyl, C$_{2-18}$ alkenyl, C$_{3-10}$ cycloalkyl, C$_{4-10}$ cycloalkenyl, C$_{1-18}$ alkoxy, —NR$^{15}$R$^{16}$, an amino acid residue linked through an amino group of the amino acid, CH$_2$OCH(=O)R$^{9a}$, or CH$_2$OC(=O)OR$^{9a}$ where R$^{9a}$ is C$_1$-C$_{12}$ alkyl, C$_6$-C$_{20}$ aryl, C$_6$-C$_{20}$ alkylaryl or C$_6$-C$_{20}$ aralkyl;

R$^{10}$ and R$^{11}$ are independently selected from the group consisting of hydrogen, C$_{1-18}$ alkyl, C$_{2-18}$ alkenyl, C$_{3-10}$ cycloalkyl, C$_{4-10}$ cycloalkenyl, aryl, —C(=O)R$^{12}$, heterocycle, or an amino acid residue;

R$^{12}$ is selected from the group consisting of hydrogen, C$_{1-18}$ alkyl, C$_{2-18}$ alkenyl, aryl, C$_{3-10}$ cycloalkyl, C$_{4-10}$ cycloalkenyl, or an amino acid residue;

R$^{15}$ and R$^{16}$ are independently selected from hydrogen, C$_{1-18}$ alkyl, C$_{2-18}$ alkenyl, C$_{2-18}$ alkynyl, aryl, C$_{3-10}$ cycloalkyl, C$_{4-10}$ cycloalkenyl, or an amino acid residue;

R$^{17}$ is independently selected from the group consisting of hydrogen, C$_{1-18}$ alkyl, C$_{2-18}$ alkenyl, C$_{2-18}$ alkynyl, C$_{1-18}$ alkoxy, C$_{1-18}$ alkylthio, C$_{1-18}$ alkylsulfoxide, C$_{1-18}$ alkylsulfone, C$_{1-18}$ halogenated alkyl, C$_{2-18}$ halogenated alkenyl, C$_{2-18}$ halogenated alkynyl, C$_{1-18}$ halogenated alkoxy, C$_{1-18}$ halogenated alkylthio, C$_{3-10}$ cycloalkyl, C$_{3-10}$ cycloalkenyl, C$_{7-10}$ cycloalkynyl, halogen, OH, CN, CO$_2$H CO$_2$R$^{18}$, NO$_2$, NR$^7$R$^8$, haloalkyl, C(=O)R$^{18}$, C(=S)R$^{18}$, SH, aryl, aryloxy, arylthio, arylsulfoxide, arylsulfone, arylsulfonamide, arylalkyl, arylalkyloxy, arylalkylthio, heterocycle, C$_{1-18}$ hydroxyalkyl, where each of said aryl, aryloxy, arylthio, arylsulfoxide, arylsulfone, arylsulfonamide, arylalkyl, arylalkyloxy, arylalkylthio, heterocycle, or C$_{1-18}$ hydroxyalkyl is optionally substituted with 1 or more R$^{19}$;

R$^{19}$ is selected from hydrogen, C$_{1-18}$ alkyl, C$_{2-18}$ alkenyl, C$_{2-18}$ alkynyl, C$_{1-18}$ alkoxy, C$_{2-18}$ alkenyloxy, C$_{2-18}$ alkynyloxy, C$_{1-18}$ alkylthio, C$_{3-10}$ cycloalkyl, C$_{4-10}$ cycloalkenyl, C$_{4-10}$ cycloalkynyl, halogen, —OH, —CN, cyanoalkyl, —NO$_2$, —NR$^{20}$R$^{21}$, C$_{1-18}$ haloalkyl, C$_{1-18}$ haloalkyloxy, —C(=O)R$^{18}$, —C(=O)OR$^{18}$, —OalkenylC(=O)OR$^{18}$, —OalkylC(=O)NR$^{20}$R$^{21}$, —OalkylOC(=O)R$^{18}$, —C(=S)R$^{18}$, SH, —C(=O)N(C$_{1-6}$ alkyl), —N(H)S(O)(O)(C$_{1-6}$ alkyl), aryl, heterocycle, C$_{1-18}$alkylsulfone, arylsulfoxide, arylsulfonamide, aryl(C$_{1-18}$)alkyloxy, aryloxy, aryl(C$_{1-18}$alkyl)oxy, arylthio, aryl(C$_{1-18}$)alkylthio or aryl(C$_{1-18}$)alkyl, where each is optionally substituted with 1 to 3 of =O, NR$^{20}$R$^{21}$, ON, C$_{1-18}$ alkoxy, heterocycle, C$_{1-18}$ haloalkyl, heterocycle alkyl, heterocycle connected to R$^{17}$ by alkyl, alkoxyalkoxy or halogen;

R$^{20}$ and R$^{21}$ are independently selected from hydrogen, C$_{1-18}$ alkyl, C$_{2-18}$ alkenyl, C$_{2-18}$ alkynyl, aryl, C$_{3-10}$ cycloalkyl, C$_{4-10}$ cycloalkenyl, —C(=O)R$^{12}$, or —C(=S)R$^{12}$;

R$^{26}$ is independently selected from hydrogen, and C$_{3-10}$ cycloalkyl;

and salts, tautomers, and stereoisomers thereof.

2. The compound of claim 1, wherein Y is a single bond and R$^1$ is phenyl substituted with 1 to 3 R$^6$.

3. The compound according to claim 1, wherein X is C1-C3 alkylene and R$^3$ is heterocycle independently substituted with 1 or 2 R$^{17}$.

4. The compound of claim 3 wherein R$^{17}$ independently is substituted with 1 or 2 R$^{19}$.

5. The compound of claim 4 wherein Y is a bond.

6. The compound of claim 4 wherein R$^1$ is aryl independently substituted with 1 or 2 R$^6$.

7. The compound of claim 4 wherein R$^2$, R$^4$ and R$^5$ are hydrogen.

8. The compound of claim 4 wherein X is methylene.

9. The compound of claim 4 wherein R$^3$ is a five membered heteroaryl containing 1 to 3 N, O and/or S ring atoms.

10. The compound of claim 4 wherein R$^3$ is isoxazolyl or pyridizinyl.

11. The compound of claim 4 wherein R$^{17}$ independently is aryl.

12. The compound of claim 11 wherein aryl is phenyl.

13. The compound of claim 12 wherein R$^{19}$ is independently halo or C1-C6 haloalkyl.

14. The compound of claim 1 wherein X is methylene and R$^3$ is isoxazole substituted with phenyl substituted with 1 or 2 R$^{19}$ independently selected from halo and C1-C6 haloalkyl.

15. The compound of claim 1 wherein R$^{26}$ is C$_3$-C$_6$ cycloalkyl.

16. The compound of claim 4 wherein R$^3$ is a six membered heteroaryl containing 1 or 2 N ring atoms.

17. A compound having the general formula:

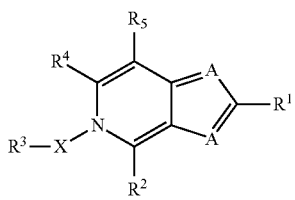

(B)

wherein:
one A is —N=, and the other A is =CR$^{26}$;
$R^1$ is phenyl or an aromatic heterocycle with 5 or 6 ring atoms with either 1, 2 or 3 N, O or S atoms in the ring, and wherein each is optionally substituted with 1 or more $R^6$;
$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{3-10}$ cycloalkynyl, or heterocycle;
X is $C_1$-$C_{10}$ alkylene, wherein 1 to 3 —CH$_2$— groups optionally are independently replaced with a heteroatom or heteroatom group selected from —O—, =O, —OR$^{27}$, —NR$^{27}$, and —N(R$^{27}$)$_2$, where $R^{27}$ independently is hydrogen, $C_{1-18}$ alkyl, $C_{2-18}$ alkenyl, or $C_{2-18}$ alkynyl;
$R^3$ is absent or is selected from hydrogen, aryl, and an aromatic heterocycle, where the aryl or heterocyclic groups are each optionally substituted with 1 or more $R^{17}$;
$R^5$ is selected from hydrogen; $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=O)OR$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocycle;
$R^6$ is selected from hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —CO$_2$R$^{18}$, NO$_2$, —NR$^7$R$^8$, $C_{1-18}$haloalkyl, C(=O)R$^{18}$, C(=S)R$^{18}$, SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$)alkylthio, heterocycle and $C_{1-18}$ hydroxyalkyl, where each is optionally substituted with 1 to 3 $R^{19}$;
$R^7$ and $R^8$ are independently selected from hydrogen, $C_{1-18}$ alkyl, $C_{1-18}$ alkenyl, aryl, $C_{3-10}$ cycloalkyl, $C_{4-10}$ cycloalkenyl, heterocycle, —C(=O)R$^{12}$; —C(=S)R$^{12}$, an amino acid residue linked through a carboxyl group thereof, or $R^7$ and $R^8$ are taken together with the nitrogen to form a heterocycle;
$R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$alkoxy, —NR$^{15}$R$^{16}$, aryl, an amino acid residue linked through an amino group of the amino acid, CH$_2$OCH(=O)R$^{9a}$, or CH$_2$OC(=O)OR$^{9a}$ where $R^{9a}$ is $C_1$-$C_{12}$ alkyl, $C_6$-$C_{20}$ aryl, $C_6$-$C_{20}$ alkylaryl or $C_6$-$C_{20}$ aralkyl;
$R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, or an amino acid residue;
$R^{15}$ and $R^{16}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, or an amino acid residue;
$R^{17}$ is independently selected from the group consisting of hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halogenated alkyl, $C_{2-18}$ halogenated alkenyl, $C_{2-18}$ halogenated alkynyl, $C_{1-18}$ halogenated alkoxy, $C_{1-18}$ halogenated alkylthio, $C_{3-10}$ cycloalkyl, $C_{3-10}$ cycloalkenyl, $C_{7-10}$ cycloalkynyl, halogen, OH, CN, CO$_2$H, CO$_2$R$^{18}$, NO$_2$, NR$^7$R$^8$, haloalkyl, C(=O)R$^{18}$, C(=S)R$^{18}$, SH, aryl, aryloxy, arylthio, arylsulfoxide, arylsulfone, arylsulfonamide, arylalkyl, arylalkyloxy, arylalkylthio, heterocycle, $C_{1-18}$ hydroxyalkyl, where each of said aryl, aryloxy, arylthio, arylsulfoxide, arylsulfone, arylsulfonamide, arylalkyl, arylalkyloxy, arylalkylthio, heterocycle, or $C_{1-18}$ hydroxyalkyl is optionally substituted with 1 or more $R^{19}$;
$R^{19}$ is selected from hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, $C_{4-10}$ cycloalkynyl, halogen, —OH, —CN, cyanoalkyl, —NO$_2$, —NR$^{20}$R$^{21}$, $C_{1-18}$ haloalkyl, $C_{1-18}$ haloalkyloxy, —C(=O)R$^{18}$, —C(=O)OR$^{18}$, —OalkenylC(=O)OR$^{18}$, —OalkylC(=O)NR$^{20}$R$^{21}$, —OalkylOC(=O)R$^{18}$, —C(=S)R$^{18}$, SH, —C(=O)N(C$_{1-6}$ alkyl), —N(H)S(O)(O)(C$_{1-6}$ alkyl), aryl, heterocycle, $C_{1-18}$alkylsulfone, arylsulfoxide, arylsulfonamide, aryl($C_{1-18}$)alkyloxy, aryloxy, aryl($C_{1-18}$ alkyl)oxy, arylthio, aryl($C_{1-18}$)alkylthio or aryl($C_{1-18}$)alkyl, where each is optionally substituted with 1 to 3 of =O, NR$^{20}$R$^{21}$, CN, $C_{1-18}$ alkoxy, heterocycle, $C_{1-18}$ haloalkyl, heterocycle alkyl, heterocycle connected to $R^{17}$ by alkyl, alkoxyalkoxy or halogen;
$R^{20}$ and $R^{21}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, —C(=O)R$^{12}$, or —C(=S)R$^{12}$;
$R^{26}$ is independently selected from hydrogen, $C_{1-18}$ alkyl, $C_{3-10}$ cycloalkyl, aryl, heterocycle, where each is optionally independently substituted with 1 to 3 of $C_{1-6}$ alkyl, $C_{1-6}$ alkoxy, halo, CH$_2$OH, benzyloxy, and OH;
and pharmaceutically acceptable salts, and stereoisomers thereof.
18. A compound having the general formula:

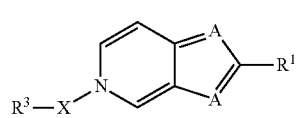

(C)

wherein:
one A is —N=, and the other A is =CR$^{26}$;
$R^1$ is phenyl optionally substituted with 1 or 2 halogens;
X is $C_1$-$C_3$ alkylene, wherein 1 or 2 —CH$_2$— groups optionally are independently replaced with —O—, =O, —OR$^{27}$, —NR$^{27}$, or —N(R$^{27}$)$_2$, where $R^{27}$ independently is hydrogen, $C_{1-6}$ alkyl, $C_{2-6}$ alkenyl, or $C_{2-6}$ alkynyl;

$R^3$ is absent or is selected from hydrogen, phenyl, and an aromatic heterocycle with 5 or 6 ring atoms with either 1, 2 or 3 N, 1 N and 1 O, or 1 or 2 N and 1 S atoms in the ring, where the phenyl or heterocyclic groups are each optionally substituted with 1 or more $R^{17}$;

$R^{17}$ is halogen, $C_{1-6}$ halogenated alkyl, or phenyl, wherein the phenyl is optionally substituted with 1 or more halogen, —$NR^{20}R^{21}$, $C_{1-6}$ alkoxy, $C_{1-6}$ haloalkyl, or $C_{1-6}$ haloalkyloxy groups;

$R^{20}$ and $R^{21}$ are independently selected from hydrogen, $C_{1-18}$ alkyl, $C_{2-18}$ alkenyl, $C_{2-18}$ alkynyl, aryl, $C_{3-10}$ cycloalkyl, or $C_{4-10}$ cycloalkenyl;

$R^{26}$ is hydrogen, cyclopentyl, or cyclohexyl;

and pharmaceutically acceptable salts, and stereoisomers thereof.

* * * * *

UNITED STATES PATENT AND TRADEMARK OFFICE
CERTIFICATE OF CORRECTION

| | | |
|---|---|---|
| PATENT NO. | : 8,263,612 B2 | Page 1 of 1 |
| APPLICATION NO. | : 11/957017 | |
| DATED | : September 11, 2012 | |
| INVENTOR(S) | : Bondy et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1203 days.

Signed and Sealed this
Twenty-sixth Day of August, 2014

Michelle K. Lee
*Deputy Director of the United States Patent and Trademark Office*